(12) United States Patent
Damm et al.

(10) Patent No.: US 6,780,972 B2
(45) Date of Patent: Aug. 24, 2004

(54) METHOD FOR THE SYNTHESIS OF PEPTIDE SALTS, THEIR USE AND THE PHARMACEUTICAL PREPARATIONS, CONTAINING PEPTIDE SALTS

(75) Inventors: Michael Damm, Rödemark (DE); Waldemar Salonek, Heidelberg (DE); Jürgen Engel, Alzenau (DE); Horst Bauer, Hersbruck (DE); Gabriele Stach, Frankfurt (DE)

(73) Assignee: Zentaris GmbH, Frankfurt (DE)

( * ) Notice: Subject to any disclaimer, the term of this patent is extended or adjusted under 35 U.S.C. 154(b) by 0 days.

(21) Appl. No.: 09/939,532

(22) Filed: Aug. 24, 2001

(65) Prior Publication Data

US 2002/0198146 A1 Dec. 26, 2002

(30) Foreign Application Priority Data

Aug. 17, 2000 (DE) .......................... 100 40 700

(51) Int. Cl.[7] .............................. C07K 1/00; C07K 1/18; C07K 7/23
(52) U.S. Cl. ................ 530/345; 530/328; 530/344; 530/402; 530/416; 514/2; 514/15
(58) Field of Search ................... 514/2, 15; 530/328, 530/344, 345, 402, 416

(56) References Cited

U.S. PATENT DOCUMENTS

| 4,431,635 A | * | 2/1984 | Coy et al. .................. 424/177 |
| 4,800,191 A | * | 1/1989 | Schally et al. ................ 51/15 |
| 5,773,032 A | * | 6/1998 | Engel et al. ................ 424/501 |
| 5,998,377 A | * | 12/1999 | Engel et al. |

FOREIGN PATENT DOCUMENTS

| EP | 0 626 170 A2 | 11/1994 |
| WO | WO99/36099 | 7/1999 |

OTHER PUBLICATIONS

Lottspeich et al., Bioanalytik, Spektrum Pub., 1998, pp. 201, 204.
Neumüller et al., Römpp's Chemical Lexicon, 1983, Franksche Publ. p. 1923, left column.

* cited by examiner

*Primary Examiner*—Brenda Brumback
*Assistant Examiner*—Anish Gupta
(74) *Attorney, Agent, or Firm*—Goodwin Procter LLP

(57) ABSTRACT

A method for producing peptide salts, including reacting an acid addition salt of a basic starting peptide in the presence of a diluent in a mixed bed ion exchanger, with a mixture of an acid and a basic ion exchanger during the formation of a free basic peptide, and then separating the ion exchanger and then the free basic peptide, with an inorganic or organic acid, and then forming the desired acid addition salt of the peptide, and removing the diluent.

5 Claims, 1 Drawing Sheet

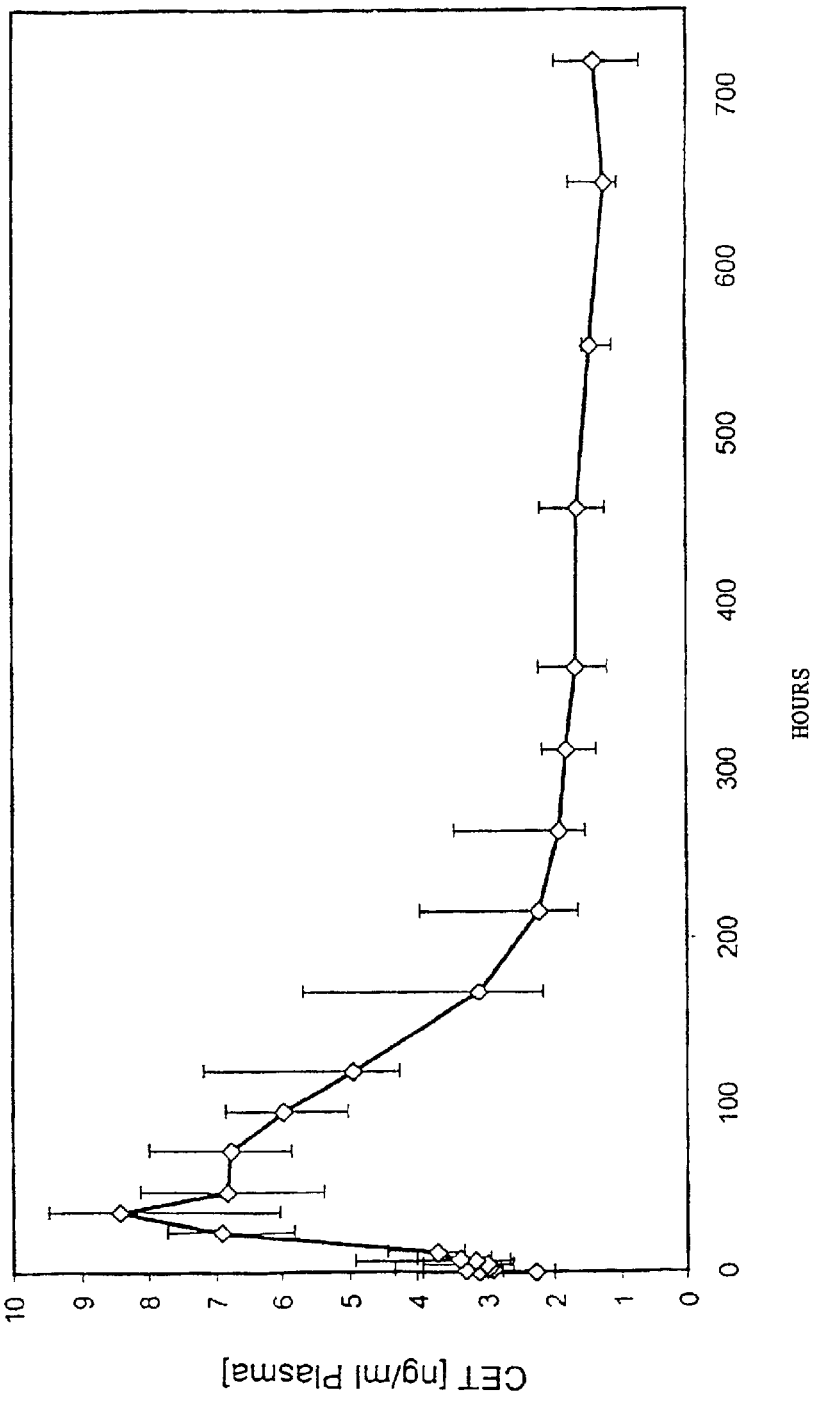

METHOD FOR THE SYNTHESIS OF PEPTIDE SALTS, THEIR USE AND THE PHARMACEUTICAL PREPARATIONS, CONTAINING PEPTIDE SALTS

The invention relates to a new method of synthesizing peptide salts, especially peptide salts of low solubility, and to their use for the preparation of pharmaceuticals. Moreover, the invention relates to pharmaceutical preparations, which contain at least one inventively synthesized peptide salt, as well as to their preparation.

In the international patent application PCT/EP 94/03904, the synthesis of a peptide of low solubility, by reacting an aqueous solution of the acid salt with an acetic acid solution of the basic peptide with precipitation of the acid addition salt of the peptide of low solubility, is described. For example, the synthesis of the LHRH antagonist, Cetrorelix embonate, is described The object of the present invention is a new method of synthesizing peptide salts, wherein an acid addition salt of a basic peptide (starting peptide salt) (1) is reacted in the presence of a suitable diluent with a mixed bed ion exchanger or with a mixture of an acidic and a basic ion exchanger with formation of the three basic peptide, the ion exchanger is subsequently removed and the free basic peptide is then reacted with an inorganic organic acid with formation of the desired acid addition salt of the peptide (final peptide salt) (2) and the diluent is subsequently removed.

The expression, basic peptide, here means poly(amino acids), also within the sense of a partial structure within a larger total structure, which has basic amino acids such as arginine, pyridylalanine or lysine, or a terminal nitrogen of a peptide or simply at least one basic group.

Preferred peptides are the LHRH antagonists, Antide, A-75998, Ganirelix, Nal-Glu antagonist, Cetrorelix, Teverelix (Antarelix[7]) as well as the antagonists of U.S. Pat. No. 5,942,493 and German patent 19911771.3, the contents of which herewith are taken up by reference. Further peptides are Abarelix, Azaline B, Detirelix, Ramorelix (Stoeckemann and Sandow, J. Cancer Res. Clin. Oncol. 1993, 119, 457) and RS-68439. The structures of the peptides named may be found in Gehre et al., GnRH antagonists; an overview, Proceedings of the $2^{nd}$ World Conference on Ovulation Induction, The Parthenon Publishing Group Ltd., Kutscher et al., Angew. Chem. 1997, 109, 2240.

The acid addition salts of the peptides, used as educts, preferably are readily soluble salts such as acetates, hydrochlorides and sulfates.

In accordance with the inventive method, the starting peptide salt is dissolved partly or completely in a diluent or suspended therein. Subsequently, a diluent is added. Solvents or diluents may be the same or different. The following, for example, come into consideration as solvents or diluents: water, ethanol, methanol, propanol, isopropanol, butanol, acetone, dimethyl ketone, methyl ethyl ketone, dimethyl acetamide, dimethylformamide, N-methylpyrollidone, lessee to the trial acetonitrile, pentane, hexane, heptane and mixtures thereof Ethanol, isopropanol or acetone are preferred. A water content of 1 to 60% and preferably of 5 to 50% is preferred.

The mixed bed ion exchanger, that is, a mixture of an acidic and a basic ion exchanger is added to the solution or suspension of the starting peptide salt. Amberlite[7], for example, comes into consideration as ion exchanger.

The amount of the ion exchanger depends on the number of basic groups per peptide. The amount is determined by the addition until a constant pH is obtained. For example, 10 grams of Amberlite MB-3 are required for 1 gram of Cetrorelix.

The pH of the solution of bases during the synthesis of the basis depends on the active ingredient used in the form of a slat, especially in the case of peptide salts with basically reacting amino acids, especially however in the case of salts of LHRH antagonists (such as Cetrorelix, D-63153, Abarelix, Ganirelix, Ramorelix, which may be present, for example, as the acetates) and is 7.5 to 13, depending on the active ingredient used.

The temperature should not exceed 25_to 30_C., in order to avoid decomposition of the peptide. The reaction time for the synthesis of the three bases usually is a few minutes, such as 20 minutes, when starting out from Cetrorelix acetate. It may, however, also be longer, such as about 1 hour, when starting out from Cetrorelix embonate. The reaction should be terminated when a constant pH is reached, since otherwise decomposition products may be formed due to the basicity of the solutions.

The ion exchanger is subsequently removed from the reaction mixture. The removal may be accomplished by sieving, filtering, centrifuging or column filtering.

The clear to cloudy solution of the free peptide base, which is unstable, should be reacted with the acid as rapidly as possible to form the desired acid addition salt. The acid may be added as a solid substance, in solution or as a suspension. The solution of the free peptide base can be added to the acid in the same way.

The reaction times can range from a few minutes to a few hours. For example, to form the cetrolix embonate, the reaction time is 1.5 hours.

Subsequently, the reaction solution, which usually is clear, is filtered sterile. After that, the solvent can be removed, the pure peptide salt being obtained. Alternatively, before the removal of the solvent, adjuvants or carriers can be added to the solution. The adjuvants can be added as solids before the sterile filtration or after the sterile filtration as a sterile filtered solution.

Mannitol, sorbitol, xylitol and soluble starch are examples of suitable adjuvants.

Pursuant to the invention, the following salts can be prepared by adding the corresponding acid: acetate, adipate, ascorbate, alginate, benzoate, benzenesulfonate, bromide, carbonate, citrate, chloride, dibutyl phosphate, dihydrogen citrate, dioctyl phosphate, dihexadecyl phosphate, fumarate, gluconate, glucuronate, glutamate, hydrogen carbonate, hydrogen tartrate, hydrochloride, hydrogen citrate, iodide, lactate, _-liponic acid, malate maleate, malonate, palmoate (embonate), palmitate, phosphate, salicylate, stearate, succinate, sulfate, tartrate, tannate, oleate, octyl phosphate.

The invention is described by the example below, without being limited to it.

EXAMPLE 1

D-20761 (46.47 g) was added in portions to 1193 g of water and dissolved with stirring (=solution 1). The solution 1 was subsequently diluted with stirring with 3261 g of 96% ethanol (=solution 2). After the dilution, solution 2 was filtered over a preliminary glass fiber filter and the filtrate was mixed by stirring with 390 g of Amberlite MB3 (mixed bed ion exchanger of strongly acidic cations and anion exchangers) (=mixture 1). Mannitol (316.8 g) was dissolved with stirring in 1267 g of water (=solution 3). After 15 minutes of stirring, the pH of the supernatant solution of mixture 1 was measured and, after a further 5 minutes of stirring the pH was measured once again. Subsequently, after a pH of 12.5 had been reached, the Amberlite MB3 was removed from the solution using a fine mesh sieve (=solution 4).

Solution 4 (4162 g) was treated with stirring with 5.34 g of embonic acid. This mixture was stirred vigorously for a further 1.5 h and the somewhat cloudy solution was subsequently filtered through a preliminary glass fiber filter. For this solution, a value of 8.4 was measured for the pH (=solution 5). The pH values were measured with a ground electrode with a viscous electrolyte liquid. The pH values were regarded only as relative values, since the solutions or suspensions measured contained ethanol and therefore indicated an apparently higher value.

Solution 5 (3333 g) was sterile filtered into the reaction apparatus, which was at room temperature, and 528 g of solution 3 was sterile filtered with stirring into solution 5, which was kept at room temperature (=solution 6).

Solution 6 was heated to 40_C. and subsequently the mixture of water and ethanol was evaporated off under vacuum to ≦1931 g (=suspension 1). The Cetrorelix embonate suspension 1 was cooled to room temperature and diluted to 3,000 g with stirring with sterile filtered water for injection purposes (=suspension 2). The finished suspension 2, adjusted to room temperature, was subsequently filled in amounts of 3.0 g into 10 mL injection flasks, which were provided with a freeze drying stopper and transferred to the freeze drying equipment.

At a plate temperature of −40_C., the injection flasks were frozen in the freeze drying equipment. The drying was carried out by means of a drying program at a plate temperature increasing from −40_C. to 20_C. The freeze-drying equipment was flooded with sterile filtered nitrogen, the injection flasks were sealed in the equipment and flanged caps were put in place and rolled.

After the freeze-drying, the sealed injection flasks were sterilized by gamma radiation at 12 kGy (min) B 15 kGy. The latter is optional.

Each injection flask contains 34.07 mg of Cetrorelix embonate, corresponding to 30 mg of Cetrorelix and 106 mg of mannitol. Water for injection purposes (2 mL) is used for the reconstitution. The suspension obtained can be administered i.m. or s.c.

Biological Effect

The Cetrorelix embonate (2:1) lyophilysate (30 mg), obtained according to Example 1, is resuspended in 2 mL of water for injection purposes and can then be administered parenterally, preferable subcutaneously (s.c.) or intramuscularly (i.m.)

For the s.c. administration, the bioavailability of the Cetrorelix embonate (2:1) is about 30 to 50% (100%= intravenously administered Cetrolix acetate). The slight or even absent burst effect in patients is a particular advantage of Cetrorelix embonate (2:1). The duration of the effect depends on the dose; for a dose of 30 to 150 mg, it is 2 to 8 weeks or longer. The inventive Cetrorelix embonate (2:1) lyophilysate has already been investigated in Clinical Phase I in man.

FIG. 1 shows the cetrorelix concentration in the plasma as a function of time (in hours) commencing with the administration of 60 mg of Cetrorelix embonate (2:1) of Example 1 in man. A burst effect (ca. 100 ng/mL) could not be detected in man. The period of action exceeded 700 hours. The plasma level was constant at about 2 ng/mL 150 hours after the administration. The bioavailability was abut 40%.

The areas of application of the inventive peptide salts are, for example, the treatment of BPH, myoma and endometriosis.

We claim:

1. A method for making a composition containing a peptide salt having a pharmaceutically acceptable anion comprising:

contacting a first peptide salt with a diluent to form a diluent solution;

contacting the diluent solution containing the first peptide salt with a mixed bed ion exchanger, wherein the mixed bed ion exchanger has strongly acidic cations and strong anion exchangers;

separating the mixed bed ion exchanger from the diluent solution;

containing the diluent solution with an acid having a pharmaceutically acceptable anion, thereby forming an acid addition salt of the peptide having the pharmaceutically acceptable anion;

adding an adjuvant to the diluent solution; and separating the diluent from the diluent solution.

2. The method of claim 1, wherein the first peptide salt is a salt of an LHRH antagonist selected from the group of Cetrorelix, Teverelix, Abarelix, Ganirelix, Azalinc B, Antide, A-75998, Detirelix, Ramorelix, and RS-68439.

3. The method of claim 1, wherein said acid is embonic acid, stearic acid, or salicylic acid.

4. The method of claim 1, wherein the first peptide salt is Cetrorelix acetate, and said acid is embonic acid, and the peptide:acid molar ratio is 2:1.

5. The method of claim 1, wherein said acid addition salt of the peptide is separated from the diluent by freeze drying.

* * * * *

UNITED STATES PATENT AND TRADEMARK OFFICE
CERTIFICATE OF CORRECTION

| | |
|---|---|
| PATENT NO. | : 6,780,972 B2 |
| APPLICATION NO. | : 09/939532 |
| DATED | : August 24, 2004 |
| INVENTOR(S) | : Damm et al. |

It is certified that error appears in the above-identified patent and that said Letters Patent is hereby corrected as shown below:

Column 4, line 33, cancel the text "containing" and replace it with --contacting--.

Signed and Sealed this

Second Day of February, 2010

David J. Kappos
*Director of the United States Patent and Trademark Office*